(12) United States Patent
Suetake et al.

(10) Patent No.: US 7,407,674 B2
(45) Date of Patent: Aug. 5, 2008

(54) LIPOLYSIS PROMOTER AND FOOD-AND-DRINK AND FEED CONTAINING THE SAME

(75) Inventors: Yoko Suetake, Saitama (JP); Keishiro Yoshida, Saitama (JP); Susumu Shimura, Saitama (JP)

(73) Assignee: Lotte Co., Ltd., Tokyo (JP)

( * ) Notice: Subject to any disclaimer, the term of this patent is extended or adjusted under 35 U.S.C. 154(b) by 0 days.

(21) Appl. No.: 11/529,126

(22) Filed: Sep. 28, 2006

(65) Prior Publication Data
US 2007/0218108 A1 Sep. 20, 2007

(30) Foreign Application Priority Data
Mar. 16, 2006 (JP) ............................. 2006-072963

(51) Int. Cl.
*A61K 36/00* (2006.01)
(52) U.S. Cl. ..................................................... 424/725
(58) Field of Classification Search ........................ None
See application file for complete search history.

(56) References Cited

U.S. PATENT DOCUMENTS

| 5,698,199 | A | 12/1997 | Mori |
| 2003/0017997 | A1* | 1/2003 | Yokota et al. ................. 514/25 |
| 2003/0036565 | A1* | 2/2003 | Parkin et al. ................. 514/683 |
| 2005/0064049 | A1 | 3/2005 | Mori |
| 2006/0134294 | A1* | 6/2006 | McKee et al. ............... 426/548 |

FOREIGN PATENT DOCUMENTS

| JP | 08-301780 | 11/1996 |
| JP | 3306750 | 7/2002 |
| JP | 2002-326947 | 11/2002 |
| JP | 2004-035516 | 2/2004 |
| JP | 3537671 | 6/2004 |

OTHER PUBLICATIONS http://www.faqs.org/health/Sick-V3/Obesity.html.*
Fugh-Berman, A. and Myers, A., *Citrius aurantium, an Ingredient of Dietary Supplements Marketed for Weight Loss*: Current Status of Clinical and Basic Research, Experimental Biology and Medicine (2004), vol. 299, pp. 698-704.

* cited by examiner

*Primary Examiner*—Susan Hoffman
*Assistant Examiner*—Catheryne Chen
(74) *Attorney, Agent, or Firm*—Scott R. Cox

(57) ABSTRACT

A naturally-derived lipolysis promoter with high safety, which may promote the degradation of the accumulated adipose tissue to control, prevent, and ameliorate obesity to a satisfactory extent, and food-and-drink and feed containing the same containing at least one or more kinds of plants selected from the group consisting of plants of the genus *Iresine* of the family Amaranthaceae, *Tipuana tipu*, *Bocconia pearcei*, *Argemone mexicana*, and *Ladenbergia magnifolia* as active ingredients, and food-and-drink and feed containing the same

7 Claims, No Drawings

LIPOLYSIS PROMOTER AND FOOD-AND-DRINK AND FEED CONTAINING THE SAME

CROSS-REFERENCE TO RELATED APPLICATION

This application claims priority from Japanese Application JP 2006-072963, filed on Mar. 16, 2006.

The present invention relates to a lipolysis promoter which promotes the degradation of body fat, reduces systemic or local fat, and is effective in preventing and ameliorating obesity, and food-and-drink and feed containing the same.

BACKGROUND OF INVENTION

Obesity results from the accumulation of intake energy in adipocytes as neutral fat in excess of consumption energy, and not only triggers various diseases such as arteriosclerosis, but also is cosmetically undesirable, so that its prevention and amelioration are strongly required. However, recent years have seen an increase in the obesity rate in the industrialized countries including our country year by year. The reason comes from overeating, lack of exercise, stress, and the like, but there are many people who cannot continue dietary restriction and exercise therapy, which require a strong will and long continuance.

This background has given rise to a wide range of development of lipolysis promoters effective in preventing and ameliorating the obesity. For example, there have been known a lipolysis promoter containing a plant or its extract selected from *Juniperus communis, Rosa normalis, Rosa canina, Areca catechu, Polygala tenuifolia, Plantago asiatica, Jateorhiza columba, Stellera chamaejasme, Tropaeolum majus, Aristolochia manshuriensis, Myrica rubra Imperata cylindrica, Ligusticum sinense, Hemerocallis plicata, Betula platyphylla* var. *japonica, Salvia miltiorrhiza, Erodium stephanianum, Brassica hirta, Helianthus annuus, Glechoma hederacea, Lycium* chinense, *Sophora japonica, Homalomena occulta, Ficus carica, Pueraria thomsonii, Hibiscus rosa-sinensis, chenopodium hybridum, Trigonella foenumgraecum, Juglans regia, Alpinia katsumadai, Prunus humilis Bunge, Gardenia jasminoides, Chrysanthemum indicum, Rubia cordifolia, Hedyotis diffusa, Lysimachia christinae, Schizonepeta tenuifolia, Portulaca oleracea, Angelica dahurica,* and *Polygonum aviculare* as an active ingredient (See Japanese Unexamined Patent Publication No. 2005-60366), a lipolysis promoter comprising an extract of *Zygophyllaceae Larrea* as an active ingredient (for example, refer to Japanese Unexamined Patent Publication No. 2004-35516), a lipolysis promoter comprising peels or leaves of citrus fruits or extracts therefrom (for example, refer to Japanese Unexamined Patent Publication No. 2002-326947), a lipolysis promoter containing a *Cirsium* plant as an active ingredient (for example, refer to Japanese Unexamined Patent Publication No. 8(1996)-301780), a lipolysis promoter containing an extract of *Geranium nepalense* Sweet (for example, refer to Japanese Patent Gazette No. 3537671), a lipolysis promoter containing *Tussilago farfara* as an active ingredient (for example, refer to Japanese Patent Gazette No. 3306750), and a lipolysis promoter containing an immature green fruit of *Piper nigrum*-L. or *Piper longum*-L. as an active ingredient (for example, refer to Japanese Patent Gazette No. 3645608). However, these lipolysis promoters cannot necessarily be said to have a sufficient effect, and some of them are concerned to cause side effects (for example, refer to Experimental Biology and Medicine (2204), Volume 229, pages 698 to 704).

With the foregoing background, there is required further development of a lipolysis promoter having a satisfying effect of preventing and ameliorating obesity, and capable of safe usage.

SUMMARY OF INVENTION

The present inventor et al. have discovered that plants of the genus *Iresine* of the family Amaranthaceae, *Tipuana tipu, Bocconia pearcei, Argemone mexicana,* and *Ladenbergia magnifolia* have an effect of promoting the degradation of neutral lipid in adipocytes, and brought the present invention to completion as a result of taking note of increased and enlarged adipocytes, which trigger obesity, and making diligent studies of various plants based on an assumption that the obesity can be prevented and ameliorated by promoting the degradation of the neutral fat in the adipocytes.

More specifically, the present invention is a lipolysis promoter containing one or more kinds of plant bodies and/or extracts therefrom selected from the group consisting of the plants of the genus *Iresine* of the family Amaranthaceae, the *Tipuana tipu,* the *Bocconia pearcei,* the *Argemone mexicana,* and the *Ladenbergia magnifolia* as the active ingredients. The present invention is also food-and-drink and feed containing the lipolysis promoter described above.

The lipolysis promoter and the food-and-drink and feed containing the same in accordance with the present invention have apparent lipolysis promoting activity in adipose tissue, and have a beneficial effect of preventing or ameliorating obesity, and reforming obese constitution.

DETAILED DESCRIPTION OF A PREFERRED EMBODIMENT

Hereinafter, the present invention will be described in detail. While a description will be given of the lipolysis promoter, the food-and-drink and feed containing the same, and the process for producing the same, as well as its efficacy in accordance with the present invention, it is to be understood that the present invention is not intended to be limited to these examples.

The lipolysis promoter of the present invention may directly contain each plant as an active ingredient, but may contain a dried product, and further a powder-processed dry product as active ingredients. In addition, it may contain extracts from each plant as active ingredients. The plant extracts may be in water, various kinds of organic solvents or liquid extracts extracted with various kinds of organic solvents containing water, or may be substances in which the liquid extracts are evaporated to dryness by a normal drying process (for example, drying under reduced pressure, freeze-drying, and the like) or concentrated by a concentrating process. The kinds of organic solvents include ethanol, methanol, acetone, ethyl acetate, and hexane, but are not particularly limited. Furthermore, the plant extracts may be subjected to purification treatment such as deodorization and decolorization within the bounds of not affecting the effectiveness thereof, as necessary.

The lipolysis promoter of the present invention can be used in any form of an oral preparation, an external preparation, and the like. Accordingly, the lipolysis promoter of the present invention may be made into an pharmaceutical preparation adapted for ease of use as an internal medicine, for example, putting the plant extracts into granules with the use of an excipient, and the like, as appropriate. Moreover, the lipolysis promoter may locally reduce fat in the face or the abdomen by direct application to the above site, and thus may be used as lotion, gel, skin lotion, an ointment, a paste, a cataplasm, a plaster, a stick agent, a sheet agent, a bath agent, a tablet for body cleaning, and the like.

The compounding amount of the lipolysis promoter of the present invention may be selected from a wide range of options though being dependent on an adding form and a dosage form. For example, in the case of the external preparation, it is preferable that the compounding amount thereof be not less than 0.005% by weight (hereinafter, expressed simply by %), particularly 0.01 to 30% by weight in a composition on a solvent extraction dried product basis. In the case of the oral preparation, it is also preferable that the compounding amount thereof be 0.01 to 10 g, particularly 0.05 to 3 g per day for adults on the solvent extraction dried product basis.

Said lipolysis promoter is compounded in the food-and-drink of the present invention, in which compoundable food and drink is not particularly limited, and may be compounded in various forms of confectionery such as chewing gum, candies, and chocolate, health food, drinks, health drinks, flavoring, bread, and noodles. The food-and-drink in accordance with the present invention may take the form of health food, functional food, or food for specified health use which is given an obesity protective effect and an obesity ameliorating effect. The food-and-drink in accordance with the present invention can also be used in general diet. And, intake of such compounded food-and-drink as described above allows amelioration of obesity and improvement in lifestyle-related disease derived from the obesity. In this case, it is preferable that the compounding amount of the lipolysis promoter be not less than 0.0001% by weight, particularly 0.01 to 99% by weight in the food-and-drink on the solvent extraction dried product basis.

Said lipolysis promoter is compounded in the feed of the present invention, in which compoundable feed is not particularly limited, and may be compounded in pet food, dairy feed, feed for hog raising, poultry feed, and the like. In this case, it is preferable that the compounding amount of the lipolysis promoter be not less than 0.0001% by weight, particularly 0.01 to 99% by weight in the feed on the solvent extraction dried product basis. And, amelioration of obesity can be achieved when pets such as dogs or cats whose obesity is becoming a problem take such compounded feed as described above in particular, and the fat content of meat can be reduced when such compounded feed as described above is further compounded in the dairy feed, the feed for hog raising, the poultry feed, and the like.

The plants used in the present invention are all commercially available as herbs.

Plants of the genus *Iresine* of the family Amaranthaceae include *Iresine angustifolia, Iresine argentata, Iresine calea, Iresine celosia, Iresine cassiniiformis, Iresine diffusa, Iresine herbstii, Iresine interrupta, Iresine lindenii, Iresine nigra, Iresine tricolor, Iresine viroid*, and *Iresine weberbaueri*. While any of these plants can be used in the present invention, the *Iresine weberbaueri* is particularly preferable. Dried flowers, flower buds, or inflorescence of the *Iresine weberbaueri* are called Flor blanca, and are being used as herbs effective for diarrhea, vomiting, inflammation of the uterus, inflammation of the stomach, renautubular infection, and ulcers.

The *Tipuana tipu* is a tree of the family Lequminosae, called Tipa, and widely used as building materials or trees lining a street, whereas the bark and leaves thereof are used as herbs effective for rheumatism and hemorrhoids.

The *Bocconia pearcei* is a plant of the family Papaveraceae, and its seeds are called Yanala and used for eye irrigation, and the like.

The *Argemone mexicana* is also a plant of the family Papaveraceae, and its flowers are called Flor cardo santo.

The *Ladenbergia magnifolia* is a plant of the family Rubiaceae, and used for a tonic, a digestive agent, a hair-growth formula, prevention or treatment of malaria, treatment of a febrile disease, and the like. Its flowers are called Flor azahar.

It should be noted that in the lipolysis promoter of the present invention, the desired sites of the plants of the genus *Iresine* of the family Amaranthaceae to be used are flowers, flower buds, inflorescence, and the like, the desired sites of the *Tipuana Tipu* to be used are bark, branches, leaves and the like, the desired sites of the *Bocconia pearcei* to be used are seeds and the like, the desired sites of the *Argemone mexicana* to be used are flowers and the like, and the desired sites of the *Ladenbergia magnifolia* to be used are also flowers and the like.

Hereinafter, while the present invention will be described in more detail with Test examples, it is to be understood that the scope of the present invention is not intended to be limited by these examples.

TEST EXAMPLE 1

The present test was carried out to obtain plant extracts from plant bodies.

1) Sample Under Test
    Nine kinds of plants shown in Table 1 were used.

2) Test Method
    To 10 g of a dried plant body, 100% ethanol, 50% ethanol or 100 ml of water was added, and extraction treatment was carried out under agitation at 70 C for 2 hours. The resultant extracts were filtered, and then subjected to vacuum concentration, followed by being freeze dried.

3) Test Result
    Each extract yield is shown in Table 1.

TABLE 1

| | Plant sample extraction rate | | |
|---|---|---|---|
| Plant name | 100% Ethanol extraction | 50% ethanol extraction | Hydrothermal extraction |
| *Iresine weberbaueri* | 6% | 12% | 11% |
| *Iresine diffusa* | 7% | 18% | 14% |
| *Iresine herbstill* | 10% | 22% | 25% |
| *Iresine lindenii* | 4% | 10% | 10% |
| *Iresine tricolor* | 7% | 15% | 12% |
| *Tipuana tipu* | 6% | 14% | 11% |
| *Bocconia pearcei* | 22% | 40% | 46% |
| *Argemone mexicana* | 12% | 49% | 42% |
| *Ladenbergia Magnifolia* | 11% | 48% | 47% |

TEST EXAMPLE 2

The present test was carried out to examine the lipolysis promoting activity of plant extracts 1) Sample Under Test
    The dried products of the 100% ethanol extracts, the 50% ethanol extracts and the water extracts, which were prepared in Test Example 1 were used.

2) Test Method (1) Adipocyte Culture

MC3T3-G2/PA6 cells, mouse-derived preadipocytes, were seeded in a 24-well plate so as to achieve $5\times10^4$ cells/well, and incubated in a 10% fetal bovine serum (FBS) adding α-MEM culture medium in the presence of 5% $CO_2$ at 37° C. Immediately before the plate becomes confluent, the culture medium was replaced by a 10% FBS α-MEM culture medium to which dexamethasone, 3-isobutyl-1-methylxanthine, and glucose were added to induce differentiation to adipocytes. The incubation was performed for 8 to 9 days after the induction, and the test was carried out after adipocyte maturation.

(2) Lipolysis Activity Measurement Method

After culture supernatant was discarded, and the well was cleaned with PBS (−), the sample and Dulbecco's Phoshate Buffered Saline containing 2% BSA and 4.5 g/L glucose were added, and incubated for 1 hour. It should be noted that the amount of the sample was adjusted so that the final concentration in this reaction system was 100 µg/ml.

After the incubation, the supernatant was sampled, and the release amount of glycerol, a lipolytic product, was measured using triglyceride E-Test Wako. The results are shown in Tables 2 to 4, provided that the release amount of the glycerol is a relative value with a control value as 100%.

Lipolysis promoting rate (%)=[A/B]×100

A: amount of released glycerol when adding the extracts

B: amount of released glycerol when adding no extracts

3) Test Results

The lipolysis promoting activity was determined on the basis of the lipolysis promoting rate shown in Tables 2 to 4, which was found from the measurements of the amount of the glycerol produced by lipolysis.

When the plant extracts under test were added, the lipolysis was apparently promoted compared with the control value.

TABLE 2

Lipolysis promoting rate of 100% ethanol extracts

| Plant material name | (%) |
|---|---|
| Iresine weberbaueri | 990% |
| Iresine diffusa | 670% |
| Iresine herbstill | 527% |
| Iresine lindenii | 402% |
| Iresine tricolor | 322% |
| Tipuana tipu | 206% |
| Bocconia pearcei | 395% |
| Argemone mexicana | 413% |
| Ladenbergia magnifolia | 478% |

TABLE 3

Lipolysis promoting rate of 50% ethanol extracts

| Plant material name | (%) |
|---|---|
| Iresine weberbaueri | 1138% |
| Iresine diffusa | 821% |
| Iresine herbstill | 907% |
| Iresine lindenii | 673% |
| Iresine tricolor | 585% |
| Tipuana tipu | 431% |
| Bocconia pearcei | 648% |
| Argemone mexicana | 601% |
| Ladenbergia magnifolia | 783% |

TABLE 4

Lipolysis promoting rate of water extracts

| Plant material name | (%) |
|---|---|
| Iresine weberbaueri | 1278% |
| Iresine diffusa | 858% |
| Iresine herbstill | 812% |
| Iresine lindenii | 701% |
| Iresine tricolor | 605% |
| Tipuana tipu | 574% |
| Bocconia pearcei | 603% |
| Argemone mexicana | 597% |
| Ladenbergia magnifolia | 622% |

TEST EXAMPLE 3

The present test was carried out to examine the lipolysis promoting activity of plant extracts in adding the plant extracts at the same time.

1) Sample Under Test

The plant extracts prepared in Test example 1 were combined as shown in Table 5, and a mixture of each plant extract in equal proportions was used.

2) Test Method (1) Adipocyte Culture

MC3T3-G2/PA6 cells, mouse-derived preadipocytes, were seeded in a 24-well plate so as to achieve $5\times10^4$ cells/well, and incubated in a 10% fetal bovine serum (FBS) adding α-MEM culture medium in the presence of 5% $CO_2$ at 37° C. Immediately before the plate becomes confluent, the culture medium was replaced by a 10% FBS α-MEM culture medium to which dexamethasone, 3-isobutyl-1-methylxanthine, and glucose were added to induce differentiation to adipocytes. The incubation was performed for 8 to 9 days after the induction, and the test was carried out after adipocyte maturation.

(2) Lipolysis Activity Measurement Method

After culture supernatant was discarded, and the well was cleaned with PBS (−), the sample and Dulbecco's Phoshate Buffered Saline containing 2% BSA and 4.5 g/L glucose were added, and incubated for 1 hour. It should be noted that the amount of the sample was adjusted so that the final concentration in this reaction system was 100 µg/ml.

After the incubation, the supernatant was sampled, and the release amount of glycerol, a lipolytic product, was measured using triglyceride E-Test Wako. The result is shown in Table 5, provided that the release amount of the glycerol is a relative value with a control value as 100%.

Lipolysis promoting rate (%)=[A/B]×100

A: amount of released glycerol when adding the extracts

B: amount of released glycerol when adding no extracts

3) Test Result

As shown in Table 5, it was confirmed that even a mixture of two or more kinds of plant extracts had high lipolysis activity compared with the control value.

TABLE 5

Effects of combination of 50% ethanol extracts on lipolysis promoting rate

| Plant material name | (%) |
|---|---|
| *Iresine weberbaueri* + *Tipuana tipu* | 923% |
| *Iresine lindenii* + *Bocconia pearcei* | 652% |
| *Iresine herbstill* + *Argemone mexicana* | 704% |
| *Tipuana tipu* + *Ladenbergia magnifolia* | 600% |
| *Bocconia pearcei* + *Ladenbergia magnifolia* | 585% |
| *Iresine lindenii* + *Tipuana tipu* + *Bocconia pearcei* | 511% |
| *Iresine herbstill* + *Tipuana tipu* + *Argemone mexicana* | 682% |
| *Iresine weberbaueri* + *Bocconia pearcei* + *Ladenbergia* + *magnifolia* | 711% |

Hereinafter, while the present invention will be described in more detail with Examples, it is to be understood that the scope of the present invention is not intended to be limited by these Examples.

EXAMPLE 1

Chewing gum was prepared according to the following formula.

| | |
|---|---|
| Gum base | 20.0 parts |
| Sugar | 55.0 parts |
| Glucose | 23.7 parts |
| Softner | 1.0 part |
| *Iresine weberbaueri* 50% ethanol extract | 0.8 parts |

EXAMPLE 2

Chewing gum was prepared according to the following formula.

| | |
|---|---|
| Gum base | 20.0 parts |
| Xylitol | 75.0 parts |
| Reduced maltose | 3.8 parts |
| Softner | 1.0 part |
| *Tipuana tipu* water extract | 0.2 parts |

EXAMPLE 3

Chewing gum was prepared according to the following formula.

| | |
|---|---|
| Gum base | 20.0 parts |
| Sugar | 55.0 parts |
| Glucose | 3.0 parts |
| Softner | 1.0 part |
| *Iresine weberbaueri* 50% ethanol extract | 0.5 parts |
| *Bocconia pearcei* 50% ethanol extract | 0.5 parts |

EXAMPLE 4

Tablet confectionery was prepared according to the following formula.

| | |
|---|---|
| Sugar | 75.0 parts |
| Lactose | 20.0 parts |
| Glycerine fatty acid ester | 0.2 parts |
| Flavor | 0.4 parts |
| *Tipuana tipu* 50% ethanol extract | 0.1 parts |
| Purified water | 4.3 parts |

EXAMPLE 5

Chocolate was prepared according to the following formula.

| | |
|---|---|
| Sugar | 41.0 parts |
| Chocolate liquor | 15.0 parts |
| Whole milk powder | 25.0 parts |
| Cocoa butter | 18.0 parts |
| Emulsifier | 0.3 parts |
| Flavor | 0.4 parts |
| *Bocconia pearcei* powder | 0.3 parts |

EXAMPLE 6

Chocolate was prepared according to the following formula.

| | |
|---|---|
| Sugar | 40.9 parts |
| Chocolate liquor | 15.0 parts |
| Whole milk powder | 25.0 parts |
| Cocoa butter | 18.0 parts |
| Emulsifier | 0.3 parts |
| Flavor | 0.4 parts |
| *Iresine herbstii* powder | 0.2 parts |
| *Argemone mexicana* powder | 0.2 parts |

EXAMPLE 7

A drink was prepared according to the following formula.

| | |
|---|---|
| Fructose-glucose liquid sugar | 5.00 parts |
| Sugar | 4.50 parts |
| Acidulant | 1.28 parts |
| Flavor | 0.20 parts |
| *Iresine weberbaueri* water extract | 0.02 parts |
| Purified water | 89.00 parts |

EXAMPLE 8

A drink was prepared according to the following formula.

| | |
|---|---|
| Orange juice | 85.25 parts |
| Sugar | 11.70 parts |
| Citric acid | 2.00 parts |
| Flavor | 1.00 part |
| *Argemone mexicana* 50% ethanol extract | 0.05 parts |

EXAMPLE 9

| A drink was prepared according to the following formula. | |
|---|---|
| Fructose-glucose liquid sugar | 5.00 parts |
| Sugar | 4.50 parts |
| Acidulant | 1.28 parts |
| Flavor | 0.20 parts |
| *Iresine lindenii* water extract | 0.01 parts |
| *Ladenbergia magnifolia* water extract | 0.01 parts |
| Purified water | 89.00 parts |

EXAMPLE 10

| An ice cream was prepared according to the following formula. | |
|---|---|
| Fructose-glucose liquid sugar | 0.5 parts |
| Sugar | 8.7 parts |
| Acidulant | 1.2 parts |
| Flavor | 0.3 parts |
| Purified water | 89.0 parts |
| Stabilizer | 0.2 parts |
| *Bocconia pearcei* water extract | 0.1 parts |

EXAMPLE 11

| Dog food was prepared according to the following formula. | |
|---|---|
| Corn | 33.0 parts |
| Flour | 35.0 parts |
| Soybean meal | 21.0 parts |
| Rice bran (defatted) | 5.5 parts |
| Meat meal | 5.0 parts |
| Mineral mix | 0.2 parts |
| *Iresine weberbaueri* powder | 0.3 parts |

EXAMPLE 12

| A capsule was prepared according to the following formula. | |
|---|---|
| *Argemone mexicana* water extract | 50.0 parts |
| Lactose | 48.0 parts |
| Magnesium stearate | 2.0 parts |

The above ingredients were uniformly mixed, and the mixed powder thereof was filled into a hard capsule.

EXAMPLE 13

| A tablet was prepared according to the following formula. | |
|---|---|
| *Argemone mexicana* 50% ethanol extract | 20.0 parts |
| *Ladenbergia magnifolia* powder | 30.0 parts |
| Lactose | 48.0 parts |
| magnesium stearate | 2.0 parts |

The above ingredients were uniformly mixed, and the mixed powder thereof was filled into a hard capsule.

EXAMPLE 14

| A tablet was prepared according to the following formula. | |
|---|---|
| *Tipuana tipu* 100% ethanol extract | 20.0 parts |
| Fine grains for direct tableting (magnesium aluminometasilicate 20%, corn starch 30%, and lactose 50%) | 48.0 parts |
| Crystalline cellulose | 30.0 parts |
| Magnesium stearate | 2.0 parts |

The above ingredients were uniformly mixed, and the mixed powder thereof was formed into a tablet of 200 mg/tablet.

EXAMPLE 15

| A tablet was prepared according to the following formula. | |
|---|---|
| *Tipuana tipu* 100% ethanol extract | 15.0 parts |
| *Bocconia pearcei* 50% ethanol extract | 5.0 parts |
| Fine grains for direct tableting (magnesium aluminometasilicate 20%, corn starch 30%, and lactose 50%) | 48.0 parts |
| Crystalline cellulose | 30.0 parts |
| Magnesium stearate | 2.0 parts |

The above ingredients were uniformly mixed, and the mixed powder thereof was formed into a tablet of 200 mg/tablet.

EXAMPLE 16

| A syrup was prepared according to the following formula. | |
|---|---|
| *Ladenbergia magnifolia* water extract | 0.1 parts |
| Simple syrup | 30.0 parts |
| Purified water | 69.9 parts |

The above plant extract was completely dissolved in the purified water, and then the simple syrup was added and mixed to obtain the corresponding syrup.

EXAMPLE 17

| A candy was prepared according to the following formula. | |
|---|---|
| *Iresine lindenii* 50% ethanol extract | 0.2 parts |
| Sugar | 50.0 parts |
| Glutinous starch syrup | 35.3 parts |
| Flavor | 0.5 parts |
| Purified water | 14.0 parts |

EXAMPLE 18

| A candy was prepared according to the following formula. | |
|---|---|
| *Iresine weberbaueri* water extract | 0.1 parts |
| *Tipuana tipu* powder | 0.2 parts |
| Sugar | 50.0 parts |
| Glutinous starch syrup | 35.2 parts |
| Flavor | 0.5 parts |
| Purified water | 14.0 parts |

EXAMPLE 19

| A biscuit was prepared according to the following formula. | |
|---|---|
| *Iresine herbstill* 50% ethanol extract | 0.5 parts |
| Flour | 50.6 parts |
| Corn Starch | 5.1 parts |
| Sugar | 12.7 parts |
| Margarine | 6.5 parts |
| Salt | 0.3 parts |
| Sodium carbonate | 1.3 parts |
| Ammonium carbonate | 0.5 parts |
| Soybean lecithin | 0.3 parts |
| Whole egg | 4.1 parts |
| Flavor | 0.3 parts |
| Purified water | 17.8 parts |

The above materials were mixed to form dough, and spread, followed by being molded and roasted in an oven to produce the corresponding biscuit.

EXAMPLE 20

| An ointment was prepared according to the following formula. | |
|---|---|
| *Iresine weberbaueri* water extract | 1.0 part |
| *Iresine herbstill* 50% ethanol extract | 1.0 part |
| Glycerine | 20.0 parts |
| Squalane | 20.0 parts |
| Cetyl alcohol | 5.0 parts |
| Magnesium stearate | 3.0 parts |
| Propylene glycol | 5.0 parts |
| Ethanol | 7.0 parts |
| Purified water | 38.0 parts |

EXAMPLE 21

| A drink was prepared according to the following formula. | |
|---|---|
| Green tea extract | 99.95 parts |
| Vitamin C | 0.01 parts |
| *Iresine weberbaueri* water extract | 0.04 parts |

EXAMPLE 22

| A drink was prepared according to the following formula. | |
|---|---|
| Oolong tea extract | 99.95 parts |
| Vitamin C | 0.01 parts |
| *Iresine herbstill* water extract | 0.04 parts |

The invention claimed is:

1. A lipolysis promoter blend comprising a lipolysis promoter active ingredient comprising a dried powdered product and/or plant extract of the genus *Iresine* of the family Amaranthaceae and the species *weberbaueri*, and an inactive ingredient.

2. The lipolysis promoter blend of claim 1 wherein the lipolysis active ingredient, further comprises water and/or an organic solvent.

3. A food-and-drink combination comprising the lipolysis promoter blend of claim 1 blended with food for ameliorating obesity.

4. A feed product for animals comprising the lipolysis promoter blend of claim 1 blended with pet food.

5. The lipolysis promoter blend of claim 1 wherein the lipolysis promoter active ingredient comprises at least 0.01% of the lipolysis promoter blend.

6. The food-and-drink combination of claim 3 wherein the lipolysis promoter active ingredient comprises at least 0.01% of the lipolysis promoter blend.

7. The feed product for animals of claim 4 wherein the lipolysis promoter active ingredient comprises at least 0.01% of the lipolysis promoter blend.

* * * * *